United States Patent [19]

Harada et al.

[11] Patent Number: 4,585,896

[45] Date of Patent: Apr. 29, 1986

[54] PROCESS FOR THE PRODUCTION OF AN AMINOPHENOL

[75] Inventors: Haruhisa Harada; Hiroshi Maki; Shigeru Sasaki, all of Chiba, Japan

[73] Assignee: Sumitomo Chemical Company, Limited, Osaka, Japan

[21] Appl. No.: 745,974

[22] Filed: Jun. 18, 1985

[30] Foreign Application Priority Data

Jun. 18, 1984 [JP] Japan ................. 59-125891
Mar. 23, 1985 [JP] Japan ................. 60-58964

[51] Int. Cl.$^4$ ............................................. C07C 85/06
[52] U.S. Cl. .................................... 564/403; 564/439
[58] Field of Search ................................ 564/403, 439

[56] References Cited

U.S. PATENT DOCUMENTS

| | | | |
|---|---|---|---|
| 2,029,642 | 6/1933 | Semon | 564/403 |
| 2,559,896 | 8/1947 | Patterson et al. | 564/403 |
| 3,845,129 | 10/1974 | Reid | 564/439 |
| 4,478,849 | 10/1984 | Ainsworth et al. | 564/439 |

FOREIGN PATENT DOCUMENTS

| | | | |
|---|---|---|---|
| 8156 | of 1890 | United Kingdom | 564/403 |
| 1028078 | 5/1966 | United Kingdom | . |
| 1228568 | 4/1971 | United Kingdom | . |
| 1291642 | 10/1972 | United Kingdom | . |
| 1324787 | 7/1973 | United Kingdom | . |
| 168710 | 11/1965 | U.S.S.R. | 564/403 |

*Primary Examiner*—Charles F. Warren
*Assistant Examiner*—R. A. Picard
*Attorney, Agent, or Firm*—Sughrue, Mion, Zinn, Macpeak and Seas

[57] ABSTRACT

In a process for the production of an aminophenol which comprises reacting a divalent phenol and ammonia in the absence of a catalyst or in the presence of a water-soluble catalyst, then separating the reaction mixture after the reaction to recover a separated and recovered product containing an aminophenol and the unreacted divalent phenol, and separating and purifying the aminophenol from said separated and recovered product, the process for the production of an aminophenol which is characterized by, on separating and purifying said aminophenol, contacting said separated and recovered product with an aliphatic ether substantially incompatible with said aminophenol in an inert gas atmosphere at a temperature at which said separated and recovered product melts or higher, then cooling to induce the crystallization of the aminophenol, thereafter filtering and recovering to obtain a cake mainly composed of said aminophenol, further melting and contacting this cake with an aliphatic ether in an inert gas atmosphere in the co-presence of water and a surfactant, and then cooling to induce the crystallization of said aminophenol and recovering it. According to the invention, a high-quality aminophenol can be produced.

6 Claims, 1 Drawing Figure

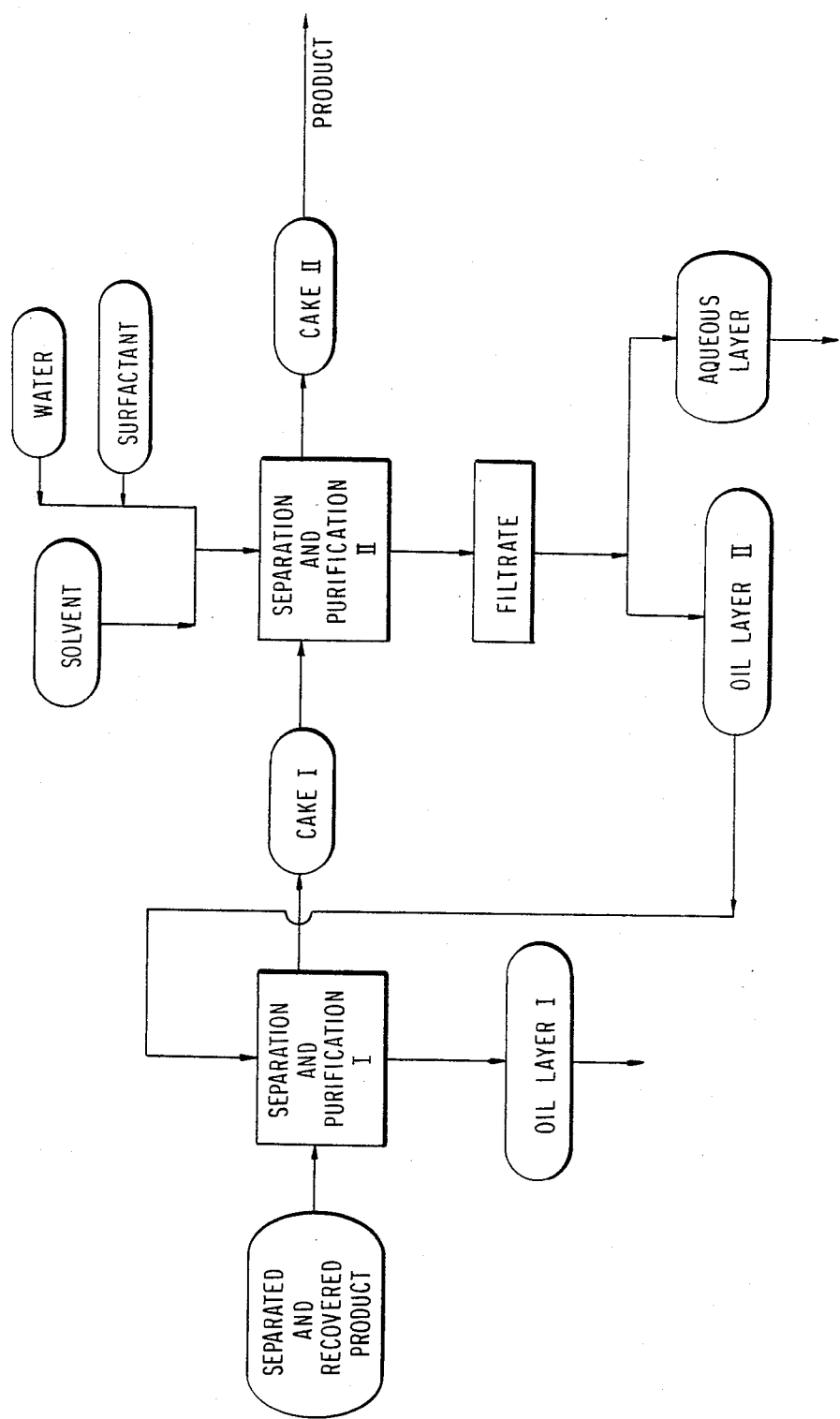

PROCESS FOR THE PRODUCTION OF AN AMINOPHENOL

FIELD OF THE INVENTION

This invention relates to a process for the production of an aminophenol by the reaction of a divalent phenol and ammonia, and more particularly to a process for the production of a high-quality aminophenol by separation and purification.

BACKGROUND OF THE INVENTION

Aminophenols are very useful compounds from an industrial point of view, which have heretofore been widely used as intermediates to medicines, agricultural chemicals, azo dyes, anti-oxidants, photographic developers, etc. and also have recently come to be used as starting materials for heat resistant resins such as polyimides or polyamides. While the process for the production of an aminophenol by reacting a divalent phenol and ammonia in the absence or presence of a catalyst is known, the reaction mixture thus obtained contained considerable amounts of the unreacted divalent phenol and by-products in addition to the end product aminophenol. Without efficiently separating these compounds, especially when the use in medicines, agricultural chemicals, etc. was contemplated, the presence of these impurities greatly hampered the successful production of high-quality medicines, agricultural chemicals, etc. Therefore, special purification steps have heretofore been necessary.

In order to obtain a purified aminophenol by separating the aminophenol from the unreacted divalent phenol and/or by-products from the reaction mixture, several methods have been proposed, for example:

(i) Japanese Patent Application (OPI) No. 28429/1973 describes a method which comprises the liquid-liquid extraction of crude aminophenol obtained by the reaction of a divalent phenol and ammonia in the absence of a catalyst, using a water-diisopropyl ether solvent. (The term "OPI" as used herein refers to a "published unexamined Japanese patent application".)

(ii) British Pat. No. 1,228,568 describes a method which comprises contacting crude p-aminophenol with a liquid aliphatic, alicyclic or aromatic ketone.

(iii) British Pat. No. 1,028,078 describes a method which comprises washing crude p-aminophenol obtained by the catalytic hydrogenation of nitrobenzene under acidic conditions, using an aliphatic alcohol, preferably isopropanol.

(iv) British Pat. No. 1,324,787 describes a method which comprises the liquid-liquid extraction of crude p-aminophenol with a solvent of benzene, toluene, xylene or an acetic acid ester and water.

(v) British Pat. No. 1,291,642 describes a method which comprises the liquid-liquid extraction of crude p-aminophenol with a solvent of carbon tetrachloride, 1,1,1-trichloroethane or 1,1-dichloroethane and water.

(vi) Japanese Patent Application (OPI) No. 69543/1980 describes a method which comprises the extraction by contacting crude p-aminophenol aqueous solution with an aromatic amine.

Then, the present inventors replicated these spreading and purifying methods and consequently found that although there was exerted a reasonable purifying effect by either method, the separation of the aminophenol from the divalent phenol and/or by-products was still inadequate and, in addition, the methods (i) to (vi) were unsatisfactory also in an aspect of the yield. In other words, in the above-described method (i), since the solubilities of both the aminophenol and divalent phenol in water are great, the separating efficiency between the aminophenol and divalent phenol is poor, and further, the loss of the aminophenol is brought about to decrease the yield, and therefore, it was economically disadvantageous. Further, since the above-described methods (ii) to (vi) are basically intended to be applied to p-aminophenol obtained by the catalytic hydrogenation of nitrobenzene under acidic conditions and hence, the by-products thereof are inherently different from those in the case of the aminophenol obtained by the reaction of the divalent phenol and ammonia, the separation of the aminophenol from the unreacted divalent phenol and/or by-products was difficult.

Therefore, the present inventors have been intensively studying on a method for its separation and purification free from the above-described drawbacks, and, as a result, have discovered that the aforesaid object may be achieved by reacting a divalent phenol and ammonia in the absence of a catalyst or in the presence of a water-soluble catalyst to obtain a reaction mixture, obtaining a separated and recovered product containing an aminophenol and the unreacted divalent phenol from the reaction mixture, contacting this separated and recovered product with an aliphatic ether substantially incompatible with the aminophenol in an inert gas atmosphere at a temperature at which the separated and recovered product melts or higher, then cooling to induce the crystallization of the aminophenol, filtering to obtain a cake mainly composed of the aminophenol, further melting and contacting this cake with an aliphatic ether in the co-presence of water and a surfactant in an inert gas atmosphere, and then cooling thereby inducing the crystallization of the aminophenol and recovering it, and thus have accomplished this invention. By this invention, it is possible to efficiently separate the aminophenol from the unreacted divalent phenol and/or by-products from the reaction mixture and moreover, the aminophenol obtained by such separation is of a high quality.

SUMMARY OF THE INVENTION

Accordingly, an object of this invention is to provide a process for the production of an aminophenol which comprises reacting a divalent phenol and ammonia in the absence of a catalyst or in the presence of a water-soluble catalyst, then separating the reaction mixture after the reaction to recover a separated and recovered product containing an aminophenol and the unreacted divalent phenol, and separating and purifying the aminophenol from said separated and recovered product, which process is characterized by, on separating and purifying said aminophenol, contacting said separated and recovered product with an aliphatic ether substantially incompatible with said aminophenol in an inert gas atmosphere at a temperature at which said separated and recovered product melts or higher, then cooling to induce the crystallization of the aminophenol, thereafter filtering and recovering to obtain a cake mainly composed of said aminophenol, further melting and contacting said cake with an aliphatic ether in an inert gas atmosphere in the co-presence of water and a surfactant, then cooling to induce the crystallization of said aminophenol and recovering its.

BRIEF DESCRIPTION OF THE DRAWING

The FIGURE is a flow sheet for the process of this invention (in which the "Solvent" stands for the "Aliphatic Ether").

DETAILED DESCRIPTION OF THE INVENTION

Specific examples of the divalent phenol used as a starting material for the reaction include catechol, resorcinol, hydroquinone, 2-methylhydroquinone, 4-methylresorcinol, 5-methylresorcinol, 5-isopropylresorcinol, 3-methylcatechol, 4-methylcatechol, 4-tert-butylresorcinol, 4-tert-butylcatechol, etc. Of these divalent phenols, it is preferred to employ a divalent phenol having no substituents, and in particular, resorcinol and hydroquinone are preferred. Further, the ammonia, which is the other starting material, may be provided either as ammonium aqueous solution or liquid ammonia. The proportion of the ammonia used is preferably in the range of from 0.5 to 10 moles per mole of the divalent phenol. With less than 0.5 mole, the formation of heavy components is increased, whereas with more than 10 moles, the burden on recovery of the ammonia is remarkable, and thus, in either case, the production of the aminophenol is markedly hampered and therefore, it is not preferred.

The reaction of the divalent phenol and the ammonia may be effected either in the absence of a catalyst or in the presence of a catalyst. As the catalyst, conventional water soluble catalysts, for example, various ammonia compounds, e.g., ammonium chloride, ammonium sulfate, ammonium phosphate, etc. are illustrated. Further, while the reaction is suitably effected in an ammonia atmosphere, it is also possible to effect it in an inert gas atmosphere of, e.g., argon, helium, nitrogen, etc.

The separated and recovered product may be obtained by separating and recovering the aminophenol and the unreacted divalent phenol from the reaction mixture after completion of the reaction. In general, said separated and recovered product also contains by-products (for example, aromatic diamines, etc.). Said separated and recovered product may be obtained, for example, by distillation, etc., as a distillate containing the aminophenol and unreacted divalent phenol from which the unreacted ammonia, water and heavy components have substantially been removed; or by distillation, etc., as a distillate containing the aminophenol and unreacted divalent phenol from which the unreacted ammonia and water have substantially been removed; or further, in the case of the reaction mixture after the reaction effected in the presence of a water-soluble catalyst, by removing most of the unreacted ammonia by distillation, etc. followed by the separation of the aqueous catalyst layer as a separated product containing the aminophenol and unreacted divalent phenol.

From the separated and recovered product containing the aminophenol and unreacted divalent phenol thus obtained, a high-purity aminophenol may be separated, purified and recovered by the process of this invention.

In the process for the production of an aminophenol according to this invention, the separated and recovered product is firstly contacted with an aliphatic ether substantially incompatible with the aminophenol while stirring and mixing in an inert gas atmosphere at a temperature at which the separated and recovered product melts or higher, and thereafter cooled while stirring to selectively induce the crystallization of the aminophenol. At that time, since the unreacted divalent phenol is soluble in the aliphatic ether, it may be efficiently separated from the aminophenol. The crystallized aminophenol may be separated by filtration, e.g., that under reduced pressure or elevated pressure, with centrifugation, etc., and if desired, may be subjected to treatment to increase the purity, such as washing with an aliphatic ether, etc.

The thus obtained cake mainly composed of the aminophenol is again contacted with an aliphatic ether while stirring and mixing in the co-presence of water and a surfactant in an inert gas atmosphere at a temperature at which the cake melts or higher, then cooled while stirring to induce the crystallization of a high-purity aminophenol. By this operation, the divalent phenol which has not been satisfactorily separated by the first operation is now removed by being dissolved in the aliphatic ether, and the by-products (for example, aromatic diamines) are removed into the aqueous layer since they are water-soluble, whereby a high-purity aminophenol crystallizes. Further, the surfactant has a remarkable effect to prevent the aminophenol from the attachment to the reactor wall on crystallization of the aminophenol. The thus crystallized aminophenol may be recovered as a cake by filtration such as that under reduced pressure or elevated pressure, with centrifugation, etc., and, if desired, may be subjected to further treatment to increase the purity such as washing with an aliphatic ether. This cake may be dried under reduced pressure according to the use purpose to give a product, and also may further be purified by distillation, etc. to give an end product.

The aliphatic ether used in this invention is one substantially incompatible with the aminophenol, and examples thereof include dichloroethyl ether, dichloroisopropyl ether, diisopropyl ether, di-n-butyl ether, diisoamyl ether, ethylene glycol diethyl ether, etc., with di-n-butyl ether and diisoamyl ether being preferred. The melting and contacting of the separated and recovered product containing the aminophenol and unreacted divalent phenol with the aliphatic ether, the crystallization of the aminophenol by cooling, the filtration and recovery thereof, the melting and contacting of the cake mainly composed of the aminophenol with the aliphatic ether in the co-presence of water and a surfactant, the crystallization of the aminophenol by cooling, and the filtration and recovery thereof are conducted in an inert gas atmosphere of, e.g., argon, helium, nitrogen, etc. Further, the aforesaid operation may be conducted either under elevated pressure, atmospheric pressure or reduced pressure, or by combination thereof depending on the melting temperature of the separated and recovered product or the cake mainly composed of the aminophenol and the boiling point of the aliphatic ether used.

The amount of water used in this invention is suitably 5 to 100 parts by weight per 100 parts by weight of the cake. With less than 5 parts by weight, the removal of the by-products is not enough, whereas with more than 100 parts by weight, the losses of the unreacted divalent phenol and aminophenol are great, and thus either is not advisable. The kind of the surfactant is not particularly restricted, and conventional ones such as cationic, anionic, amphoteric and nonionic surfactants may be used. Of these, the nonionic surfactants are preferably used. The amount thereof used is suitably 0.005 to 5 parts by weight per 100 parts by weight of the cake, and with 0.005 part by weight, the effect is not enough, whereas even if more than 5 parts by weight is used, the effect is not increased, and thus it is not advisable.

The separation and purification of this invention are efficiently conducted as shown in the FIGURE by using an oil layer in series. That is, in Separation and Purification I, Oil Layer II recovered from Sepration and Purification II and Separated and Recovered Product are melted and contacted with each other in an inert gas atmosphere, then cooled, and thereafter subjected to filtration to obtain Cake I mainly composed of an aminophenol. Thereafter, in Separation and Purification II, this Cake I is melted and contacted either with Aliphatic Ether recovered from Oil layer I by distillation, etc. or with a fresh aliphatic ether in an inert gas atmosphere, then cooled and thereafter subjected to filtration to obtain Cake II composed of a high-purity aminophenol. Filtrate is separated into Oil Layer II and Aqueous Layer, and Oil Layer II is reused in Separation and Purification I. The mixture containing the unreacted divalent phenol obtained after recovering the aliphatic ether, etc. from Oil layer I by distillation, etc. may be recycled to and reused in the reaction system.

This invention is more particularly described by the following examples, but it should be noted that this invention be not restricted by these examples.

EXAMPLE 1

(1) 110 g (1.0 mol) of resorcinol and 91.2 g (1.5 moles as ammonia) of a 28% ammonium aqueous solution were charged in a 500 cc stainless steel autoclave (equipped with a rotating stirrer), then, after displacing the inside atmosphere by nitrogen, heated to 240° C. and the amination reaction was effected for 3 hours. After completion of the reaction, the excess ammonia was removed by purging while cooling, whereby the reaction mixture was taken out. Gas chromatography (hereinafter referred to as GC) analysis revealed that it contained 44.0 g of recorcinol and 55.7 g of m-aminophenol.

This reaction mixture was transferred to a 300 cc three-necked eggplant type flask, then the water was distilled off under a reduced pressure of 100 mmHg, and subsequently, heavy components were distilled off at 5 mmHg. The distilled resorcinol and m-aminophenol were, as the result of GC analysis, 41.8 g and 53.0 g, respectively.

Thereafter, this distillate and 200 g of di-n-butyl ether as a solvent were charged in a one-liter separable flask, and contacted with each other while keeping the distillate in a molten state in a nitrogen stream at 120° C. for 15 minutes followed by cooling to 30° C. thereby inducing the crystallization of m-aminophenol. The formed crystals were separated from the filtrate by filtration, then 200 g of fresh di-n-butyl ether was charged, melted and contacted with each other at 120° C. for 15 minutes followed by a procedure similar to that for the first time, thereby obtaining crystals of m-aminophenol. The weight of the crystals after drying at 60° C. under reduced pressure was 45.3 g, and the purity of m-aminophenol was 99.3%.

(2) The whole of the di-b-butyl ether layer after separating the m-aminophenol obtained in the above-described (1) was distilled under a reduced pressure of 200 mmHg to remove the solvent, whereby the unreacted resorcinol was recovered. The obtained distillation bottoms contained 41.7 g of resorcinol and 7.9 g of m-aminophenol. 68.3 g of fresh resorcinol was added to this recovered resorcinol, 91.2 g of a 28% ammonium aqueous solution was added thereto, and, after displacing the inside atmosphere by nitrogen, the amination reaction was effected at 240° C. for 3 hours. Thereafter, procedures similar to those in the above-described (1) were conducted to obtain a reaction mixture. GC analysis revealed that it contained 44.5 g of resorcinol and 63.1 g of m-aminophenol, thus it was possible to reproduce the first reaction.

EXAMPLE 2

(1) Procedures similar to those in Example 1 were conducted except that the solvent in Example 1 was replaced by 200 g of diisoamyl ether, to obtain 46.0 g of crystals of m-aminophenol having a purity of 98.8%. Further, these crystals were distilled under a reduced pressure of 5 mmHg to obtain 42.3 g of m-aminophenol having a purity of 99.9%.

(2) The diisoamyl ether layer obtained in the above-described (1) was subjected to procedures similar to those in Example 1 to recover 40.8 g of resorcinol and 7.5 g of m-aminophenol, to which 69.2 g of fresh resorcinol and 91.2 g of a 28% ammonium aqueous solution were added, and thereafter, the reaction was effected in a manner similar to that in Example 1 to obtain a reaction mixture. As the result of GC analysis, it contained 44.2 g of resorcinol and 62.8 g of m-aminophenol, thus it was possible to reproduce the first reaction.

COMPARATIVE EXAMPLE 1

A distillate obtained by procedures similar to those in Example 1 (containing 41.8 g of resorcinol and 53.0 g of m-aminophenol) was dissolved in 100 g of water at 70° C., extracted twice with 200 g of di-n-butyl ether at the same temperature to obtain an aqueous layer, and then cooled to 20° C. to induce the crystallization of m-aminophenol. The formed crystals were recovered by filtration and dried under reduced pressure at 60° C. to obtain 38.8 g of crystals of a purity of 93.2%. It was evident that the process of this invention is extremely superior in the purity and recovery of m-aminophenol.

EXAMPLE 3

(1) 110 g (1.0 mole) of hydroquinone and 91.2 g (1.5 moles as ammonia) of a 28% ammonium aqueous solution were charged in a 500 cc stainless steel autoclave (equipped with a rotating stirrer), then, after displacing the inside atmosphere by nitrogen, heated to 240° C. and the amination reaction was effected for 2 hours. After completion of the reaction, the excess ammonia was removed by purging while cooling, whereby the reaction mixture was taken out. GC analysis revealed that it contained 32.6 g of hydroquinone and 57.8 g of p-aminophenol.

This reaction mixture was transferred to a 300 cc three-necked eggplant type flask, then the water was distilled off under a reduced pressure of 200 mmHg, and subsequently, heavy components were distilled off at 2 mmHg. The distilled hydroquinone and p-aminophenol were, as the result of GC analysis, 30.8 g and 53.1 g, respectively.

Thereafter, this distillate and 300 g of diisoamyl ether as a solvent were charged in a one-liter separable flask, and contacted with each other while keeping the distillate in a molten state in a nitrogen stream at 170° C. for 15 minutes followed by cooling to 30° C. thereby inducing the crystallization of p-aminophenol. The formed crystals were separated from the filtrate by filtration, then 300 g of fresh diisoamyl ether was charged, melted and contacted with each other at 170° C. for 15 minutes followed by a procedure similar to that for the first time, thereby obtaining crystals of p-aminophenol. The weight of the crystals after drying at 60° C. under reduced pressure was 44.1 g, and the purity of p-aminophenol was 99.4%.

(2) The whole of the diisoamyl ether layer after separating the p-aminophenol obtained in the above-described (1) was distilled under a reduced pressure of 200 mmHg to remove the solvent, whereby the unreacted hydroquinone was recovered. The obtained distillation bottoms contained 29.8 g of hydroquinone and 8.9 g of p-aminophenol. 80.2 g of fresh hydroquinone was added to this recovered hydroquinone, 91.2 g of a 28% ammonium aqueous solution was added thereto, and, after displacing the inside atmosphere by nitrogen, the amination reaction was effected at 240° C. for 2 hours. Thereafter, procedures similar to those in Example 1 were conducted to obtain a reaction mixture. As a result of GC analysis, it contained 31.8 g of hydroquinone and 66.3 g of p-aminophenol, thus it was possible to reproduce the first reaction.

EXAMPLE 4

110 g (1.0 mole) of resorcinol and 75.9 g (1.25 moles as ammonia) of a 28% ammonium aqueous solution were charged in a 500 cc stainless steel autoclave (equipped with a rotating stirrer), then, after displacing the inside atmosphere by nitrogen, heated to 230° C. and the amination reaction was effected for 5 hours. After completion of the reaction, the excess ammonia was purged by depressurizing with cooling, whereby the reaction mixture was taken out. This was then transferred to a 300 cc three-necked eggplant type flask, then the remaining ammonia and water were substantially distilled off under a reduced pressure of 100 mmHg to obtain a separated and recovered product. As the result of liquid chromatography (hereinafter referred to as LC) analysis, 43.5 g of resorcinol, 54.3 g of m-aminophenol and 1.8 g of m-phenylenediamine as a by-product were contained therein.

Thereafter, this separated and recovered product and 200 g of a solvent di-n-butyl ether (containing 0.5% by weight of resorcinol) were charged in a one-liter separable flask, and contacted with each other while keeping this separated and recovered product in a molten state in a nitrogen stream at 100° C. for 15 minutes followed by cooling to 30° C. thereby inducing the crystallization of m-aminophenol. The formed m-aminophenol was filtered using a centrifugal filter (manufactured by Sanyo Rikagaku Co., Model 10A, 3000 rpm; this also applies hereinafter) to obtain a cake mainly composed of m-aminophenol. Further, this cake, 200 g of a fresh solvent di-n-butyl ether (containing 0.5% by weight of resorcinol), 30 g of water and 0.1 g of a surfactant (Emulgen 905 produced by Kao Atlas Co., Ltd.) were charged, melted and contacted at 90° C. for 15 minutes followed by procedures similar to those for the first time to obtain a cake composed of m-aminophenol. On cooling in the second operation, the attachment of the m-aminophenol to the reactor wall was hardly recognized.

Then, this cake was distilled under reduced pressure to obtain 45.7 g of a product m-aminophenol. The purity of this m-aminophenol was 99.7%.

EXAMPLE 5

The amination reaction was effected under the same conditions as in Example 4, then water was distilled off under a reduced pressure of 100 mmHg and subsequently heavy components were distilled off under a reduced pressure of 5 mmHg. The obtained distillate contained, as the result of LC analysis, 42.9 g of resorcinol, 53.7 g of m-aminophenol and 1.6 g of m-phenylenediamine as a by-product.

Thereafter, this distillate was subjected to the separation and purification of the m-aminophenol by procedures similar to those in Example 4.

First, 250 g of a solvent di-n-butyl ether (fresh solvent) and the above distillate were melted and contacted with each other in a nitrogen seal at 105° C. for 15 minutes followed by cooling to 30° C. to induce the crystallization of m-aminophenol, after which centrifugal filtration was conducted to obtain a cake mainly composed of m-aminophenol. Further, this cake, 250 g of a solvent di-n-butyl ether (fresh solvent), 25 g of water and 0.1 g of a surfactant (Tween 20 produced by Kao Atlas Co., Ltd.) were charged, melted and contacted at 90° C. for 15 minutes followed by the procedures similar to those for the first time to obtain a cake of m-aminophenol. On cooling in the second operation, the attachment of the m-aminophenol to the reactor wall was hardly recognized. This cake was dried under reduced pressure at 60° C. to obtain 46.1 g of a product m-aminophenol. The purity of this m-aminophenol was 99.8%.

EXAMPLE 6 AND COMPARATIVE EXAMPLES 2 TO 4

Using a distillate obtained by procedures similar to those in Example 5 (containing 43.2 g of resorcinol, 54.0 g of m-aminophenol and 1.8 g of m-phenylenediamine), the effects of the water and the surfactant in the second operation were studied. The procedures for the separation and purification were the same as in Example 5 except that 200 g of di-n-butyl ether (fresh solvent) was used. The results are shown in Table 1.

TABLE 1

| | Amount of Water Added (g) | Amount of Surfactant Added (g) | Amount of m-Aminophenol Recovered (g) | Purity of m-Aminophenol (%) | Attachment to Reactor Wall |
|---|---|---|---|---|---|
| Example 6 | 25 | 0.1 | 46.4 | 99.8 | Almost none |
| Comparative Example 2 | 0 | 0.1 | 47.8 | 99.3 | Attached |
| Comparative Example 3 | 25 | 0 | 46.5 | 99.7 | Attached |
| Comparative Example 4 | 125 | 0.1 | 30.3 | 99.9 | Almost none |

COMPARATIVE EXAMPLE 5

Procedures similar to those in Example 5 were conducted except that the nitrogen seal was not employed on the separation and purification, to find that the obtained cake composed of m-aminophenol was changed to dark brown.

While the invention has been described in detail and with reference to specific embodiments thereof, it will be apparent to one skilled in the art that various changes and modifications can be made therein without departing from the spirit and scope thereof.

What is claimed is:

1. In a process for the production of an aminophenol which comprises reacting a divalent phenol and ammonia in the absence of a catalyst or in the presence of a water-soluble catalyst, then separating the reaction mixture after the reaction to recover a separated and recovered product containing an aminophenol and the unreacted divalent phenol, and separating and purifying the aminophenol from said separated and recovered product, the process for the production of an aminophenol which is characterized by, on separating and purifying said aminophenol, contacting said separated and recovered product with an aliphatic ether substantially incompatible with said aminophenol in an inert gas atmosphere at a temperature at which said separated and recovered product melts or higher, then cooling to induce the crystallization of the aminophenol, thereafter filtering and recovering to obtain a cake mainly composed of said aminophenol, further melting and contacting this cake with an aliphatic ether in an inert gas atmosphere in the co-presence of water and a surfactant, and then cooling to induce the crystallization of said aminophenol and recovering it.

2. A process for the production of an aminophenol according to claim 1, wherein said aliphatic ether is di-n-butyl ether or diisoamyl ether.

3. A process for the production of an aminophenol according to claim 1, wherein the amount of the water present is 5 to 100 parts by weight and that of the surfactant is 0.005 to 5 parts by weight, per 100 parts by weight of said cake, respectively.

4. A process for the production of an aminophenol according to claim 1, wherein said divalent phenol is resorcinol or hydroquinone.

5. A process for the production of an aminophenol according to claim 1, wherein said surfactant is a nonionic surfactant.

6. A process for the production of an aminophenol according to claim 1, wherein the mixture containing the unreacted divalent phenol which has been obtained by distilling off the aliphatic ether from the mixture of the divalent phenol, the water and the aliphatic ether obtained after the crystallization and separation of the aminophenol is recycled to and reused in the reaction system.

* * * * *